United States Patent
Tsai

[19]

[11] Patent Number: 6,149,038
[45] Date of Patent: Nov. 21, 2000

[54] SUIT HANGER WITH AIR FRESHENER

[76] Inventor: Sam Tsai, 4F, No. 14, Lane 281, Sec. 2, Hsi Yuan Road, Taipei, Taiwan

[21] Appl. No.: 09/524,413

[22] Filed: Mar. 11, 2000

[51] Int. Cl.[7] .................................................... A47G 25/14
[52] U.S. Cl. .................................. 223/86; 223/85; 223/94
[58] Field of Search .................................. 223/85, 94, 89, 223/86, 92; 239/34, 57

[56] References Cited

U.S. PATENT DOCUMENTS

| | | | |
|---|---|---|---|
| 2,354,099 | 7/1944 | Bess | 223/86 |
| 2,529,294 | 11/1950 | Hammond, Jr. | 223/86 |
| 2,582,669 | 1/1952 | Battle | 223/86 |
| 2,601,074 | 6/1952 | Walton | 223/86 |
| 5,538,166 | 7/1996 | Ogawa et al. | 223/85 |

*Primary Examiner*—Bibhu Mohanty

[57] ABSTRACT

A suit hanger includes a central casing in which an air freshener is housed and two arms attached to opposite sides of the central casing. The central casing defines at least one air inlet opening for drawing air into the air freshener to generate cleaned air. Each arm defines at least one air outlet opening in communication with the air freshener for driving the cleaned air into clothes hung by the suit hanger thereby deodorizing the clothes. A hook is removably attached to the central casing for hanging the suit hanger on a cross bar. The arms are movable with respect to the central casing between a filly expanded position and a collapsed position and at least a partially expanded position therebetween for hanging clothes of different sizes. The arms may also be inserted into shoes for supplying the cleaned into and thus deodorizing the shoes. The suit hanger may also serve as a stand-alone air freshener by removing clothes or shoes from the arms whereby the cleaned air is allowed to be supplied into the environments.

9 Claims, 6 Drawing Sheets

SUIT HANGER WITH AIR FRESHENER

FIELD OF THE INVENTION

The present invention generally relates to a suit hanger, and in particular to a suit hanger with an air freshener which deodorizes clothes hung by the hanger.

BACKGROUND OF THE INVENTION

Clothes are usually hung inside a closet by means of suit hangers. Conventionally, a suit hanger only serves to hang clothes. Clothes, especially jackets or coated, are frequently contaminated by different kinds odors, such as smoke, sweat, drink, food or dirt. Without properly treated, lingering odors may be full of a closet in which the contaminated clothes are placed. This is undesired.

Thus, it is desired to provide a suit hanger which is capable to remove odors caused by contamination contained in the fabrics of a suit for overcoming the above problem.

SUMMARY OF THE INVENTION

Accordingly, an object of the present invention is to provide a suit hanger which comprises an air freshener for removes odors from the fabrics of clothes.

Another object of the present invention is to provide a suit hanger having movable arms which can be pivotally fixed at different angular positions for hanging clothes of different sizes.

A further object of the present invention is to provide a suit hanger with an air freshener, the suit hanger being capable to be collapsed to a compact shape for serving as a stand-alone air freshener for a closed space, such as a closet.

Yet a further object of the present invention is to provide an air freshener which is capable to be inserted into a shoe for cleaning and deodorizing the shoe.

A further object of the present invention is to provide a multi-purpose air freshening device which can deodorize different articles and also work as a standalone air freshening device.

To achieve the above objects, in accordance with the present invention, there is provided a suit hanger comprising a central casing in which an air freshener is housed and two arms attached to opposite sides of the central casing. The central casing defines at least one air inlet opening for drawing air into the air freshener to generate cleaned air. Each arm defines at least one air outlet opening in communication with the air freshener for driving the cleaned air into clothes hung by the suit hanger thereby deodorizing the clothes. A hook is removably attached to the central casing for hanging the suit hanger on a cross bar. The arms are movable with respect to the central casing between a fully expanded position and a collapsed position and at least a partially expanded position therebetween for hanging clothes of different sizes. The arms may also be inserted into shoes for supplying the cleaned into and thus deodorizing the-shoes. The suit hanger may also serve as a stand-alone air freshener by removing clothes or shoes from the arms whereby the cleaned air is allowed to be supplied into the environments.

BRIEF DESCRIPTION OF THE DRAWINGS

The present invention will be apparent to those skilled in the art by reading the following description of a preferred embodiment thereof, with reference to the accompanying drawings, in which.

DETAILED DESCRIPTION OF THE PREFERRED EMBODIMENT

Figure 1:
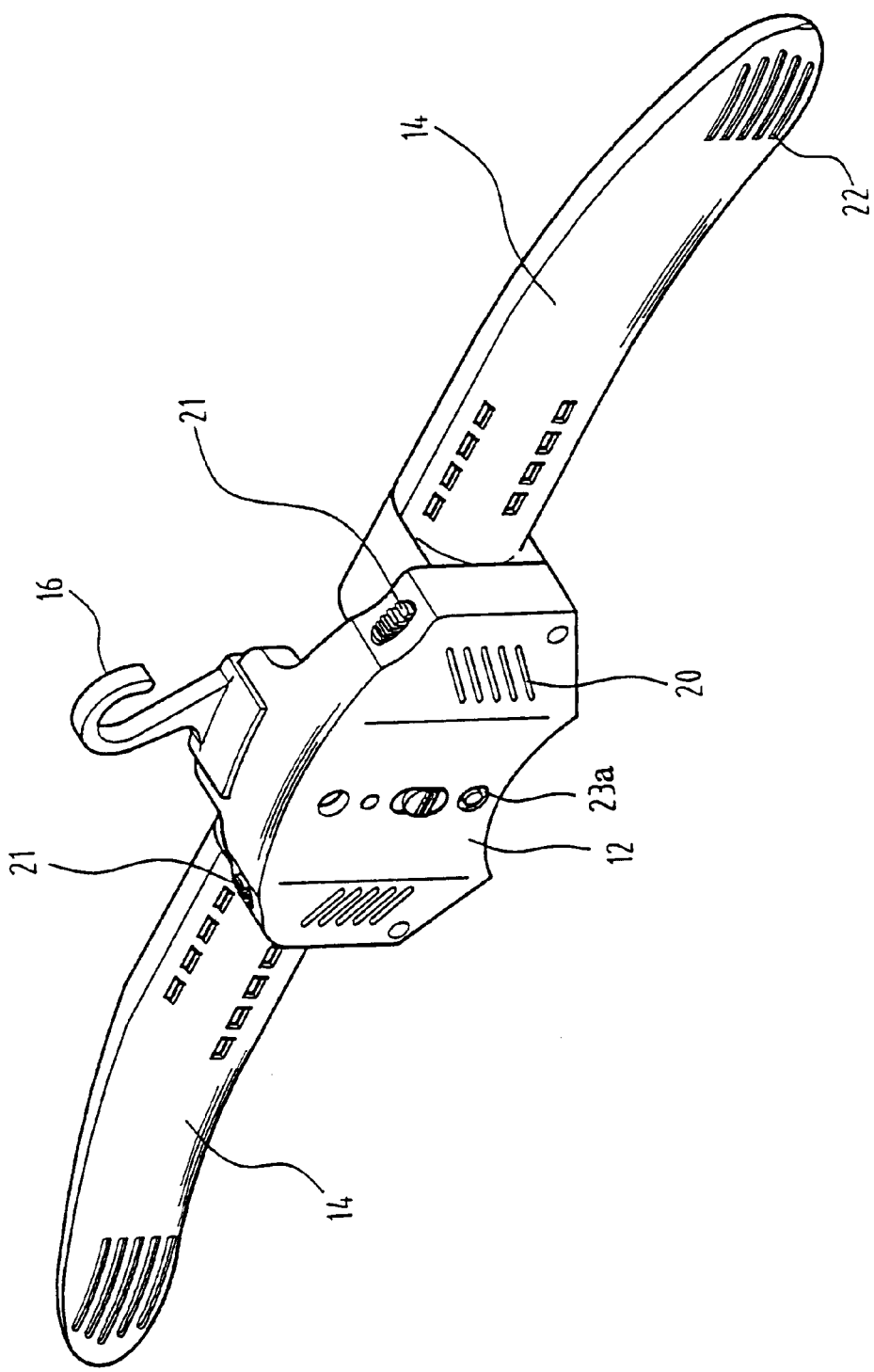
FIG. 1 is a perspective view of a suit hanger in accordance with the present invention at a fully expanded position.
Figure 2:
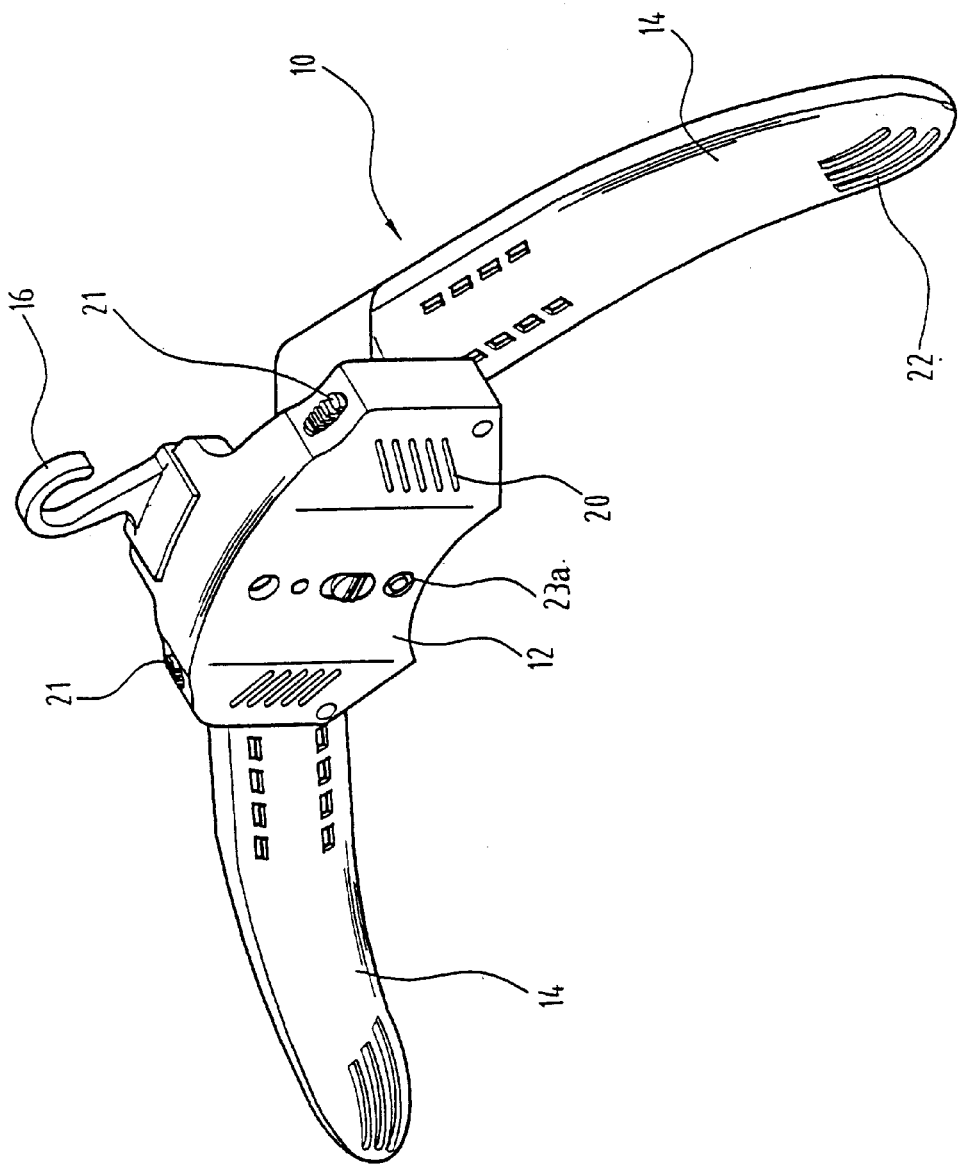
FIG. 2 is a perspective view of the suit hanger of the present invention at a partially expanded position.
Figure 3:
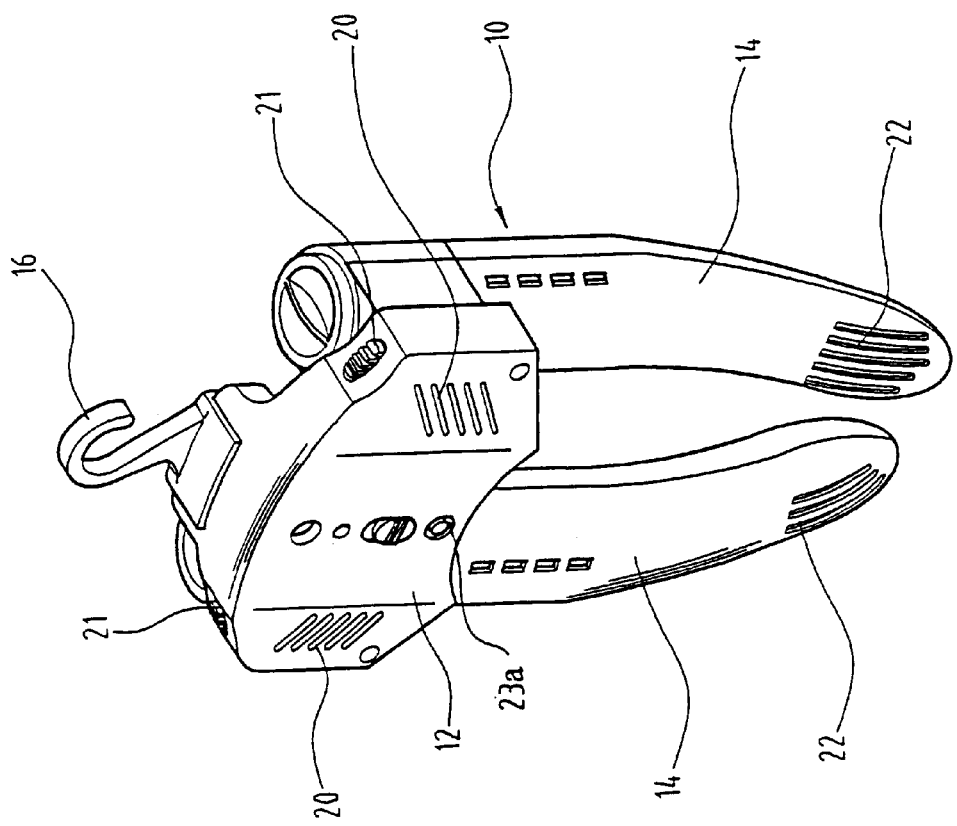
FIG. 3 is a perspective view of the suit hanger of the present invention at a collapsed position.

With reference to the drawings and in particular to FIGS. 1–3, wherein a suit hanger constructed in accordance with the present invention, generally designated with reference numeral 10, is shown, the suit hanger 10 comprises a central casing 12 and two arms 14 extending from opposite sides of the central casing 12. A hook 16 is attached to the central casing 12 for hanging the suit hanger on a cross bar 18 in a closet (see FIG. 5). Preferably, the hook 16 is removably attached to the central casing 12.

Figure 4:
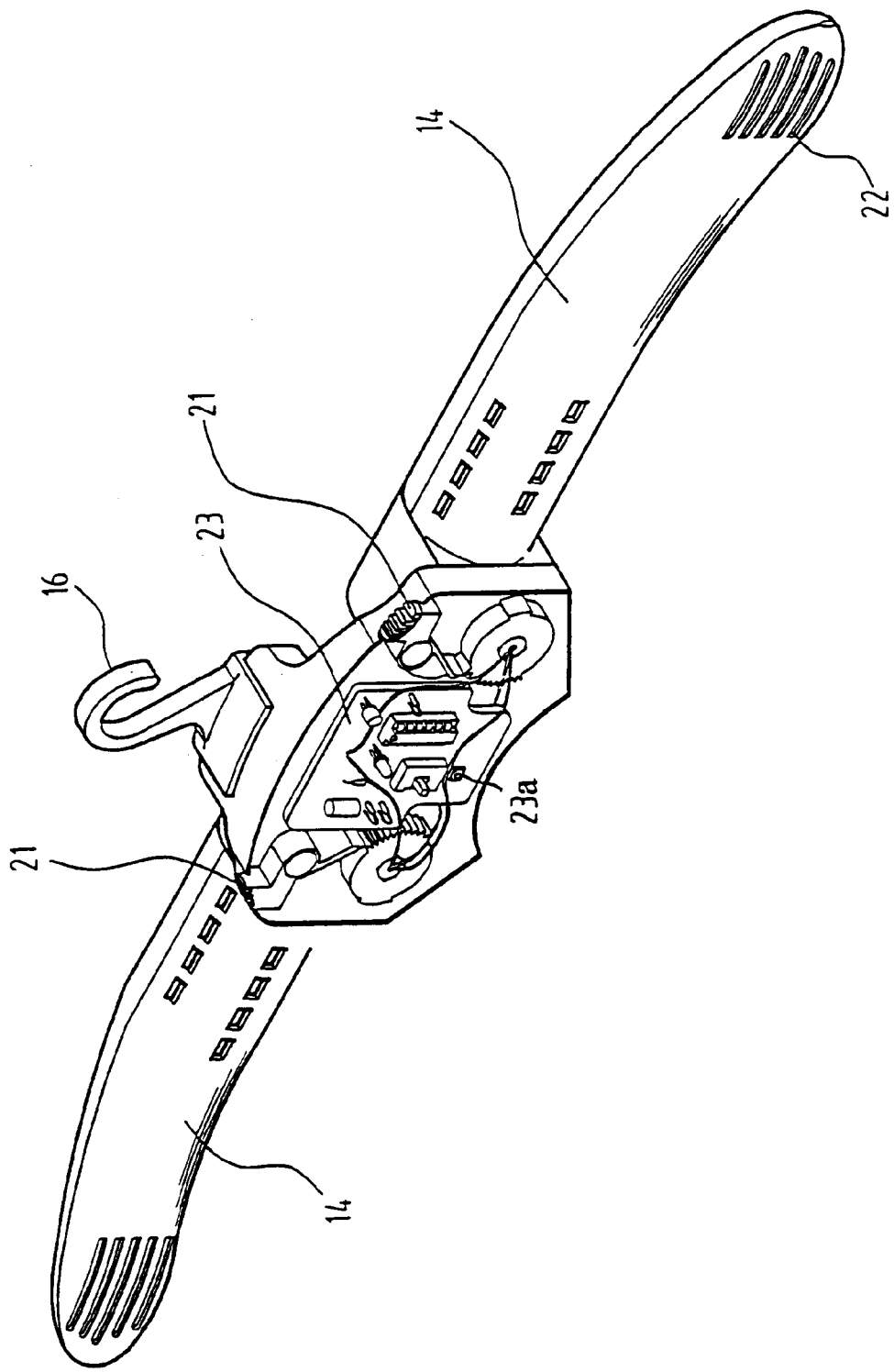
FIG. 4 is a perspective view showing the suit hanger of the present invention when removing some parts of the central casing.

As shown in FIG. 4, an air freshener means 23 is housed in the central casing 12. Inlet openings 20 are defined in the central casing 12 for drawing air into the air freshener means. The air freshener means 23 may comprise an ionic freshener which is capable to refreshing air. For example, the air freshener may generate ozone for cleaning and disinfecting air. The air freshener means 23 may be operated by a built-in power source, such as a battery set, or powered by an external power source. Furthermore, an air freshener means 23 may have a timer switch 23a (shown in FIG. 1–4) which controls the operation of the electric air freshener for a interval of time(e.g. 3 minutes). Such an air freshening technique is well known and will not be further described.

The arms 14 are pivotally attached to the central casing 12. Positioning means 21 is provided to pivotally fix the arms 14 at multistage angular positions with respect to the central casing 12. In the embodiment illustrated, the arms 14 are allowed to be moved from a fully expanded position as shown in FIG. 1 to a partially expanded position as shown in FIG. 2 and finally to a collapsed position shown in FIG. 3. The fully expanded position and the partially expanded position allow the suit hanger 10 to hang clothes of different sizes. Of course, there may be more than one partially expanded position between the fully expanded position and the collapsed position.

Each arm 14 defines air outlet openings 22 which are in communication with the air freshener means housed in the central casing 12 via passageways formed inside or outside the arms 14 whereby cleaned air is forced into the clothes fit over the suit hanger 10 via the outlet openings 22 to clean and deodorize the fabrics of the clothes. Preferably, the outlet openings 22 are adjacent free ends of the arms 14. Each arm 14 may has inner space which accommodates at least one battery (not shown) as a built-in DC power source.

Figure 5:
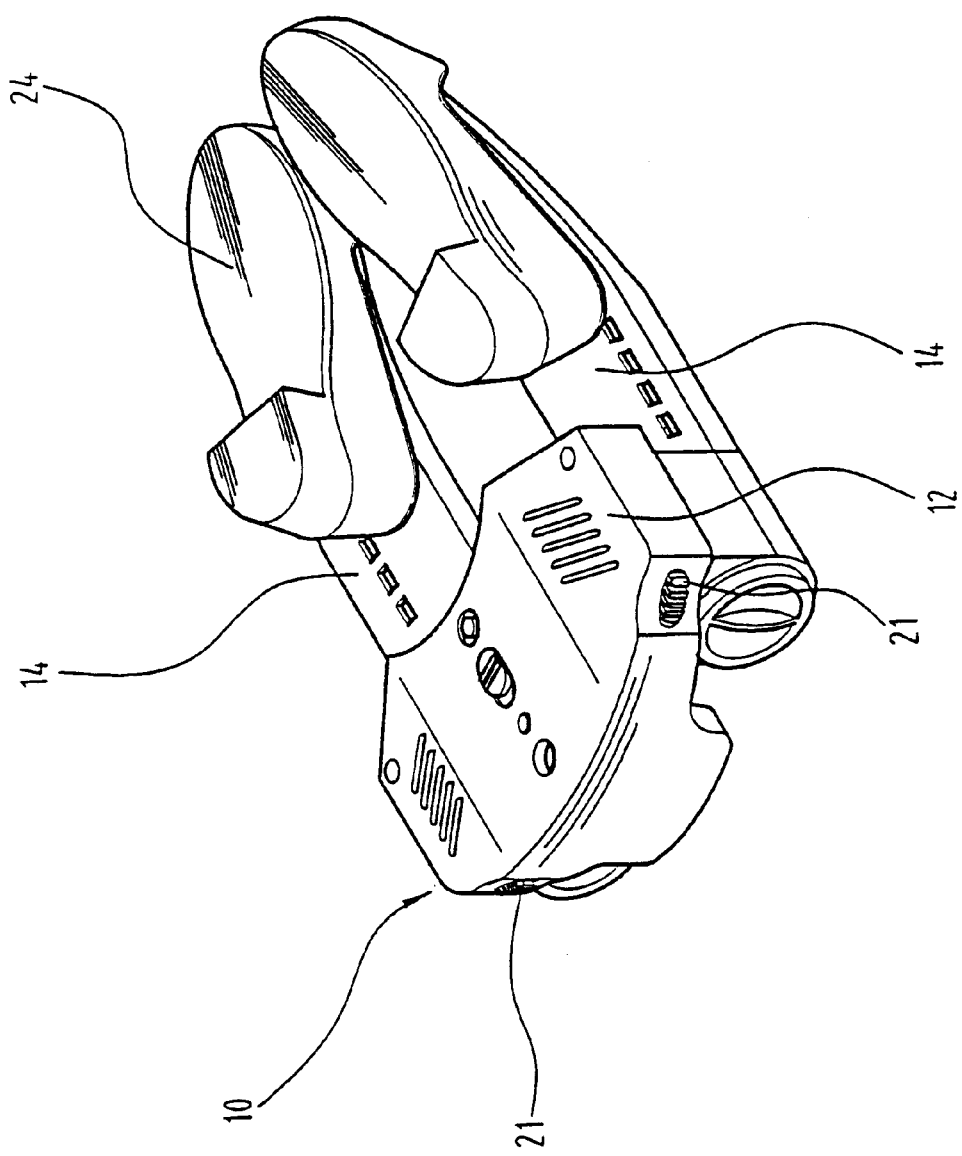
FIG. 5 is a perspective view showing the suit hanger of the present invention serving as a shoe freshener.

FIG. 5 shows another application of the suit hanger with air freshener of the present invention wherein the arms 14 of the suit hanger 10 are respectively inserted into two shoes 24 for driving cleaned air into the shoes 24 for destroying odors and killing fungus, mold, mildew and bacteria. In this application, the hook 16 is removed.

Figure 6:
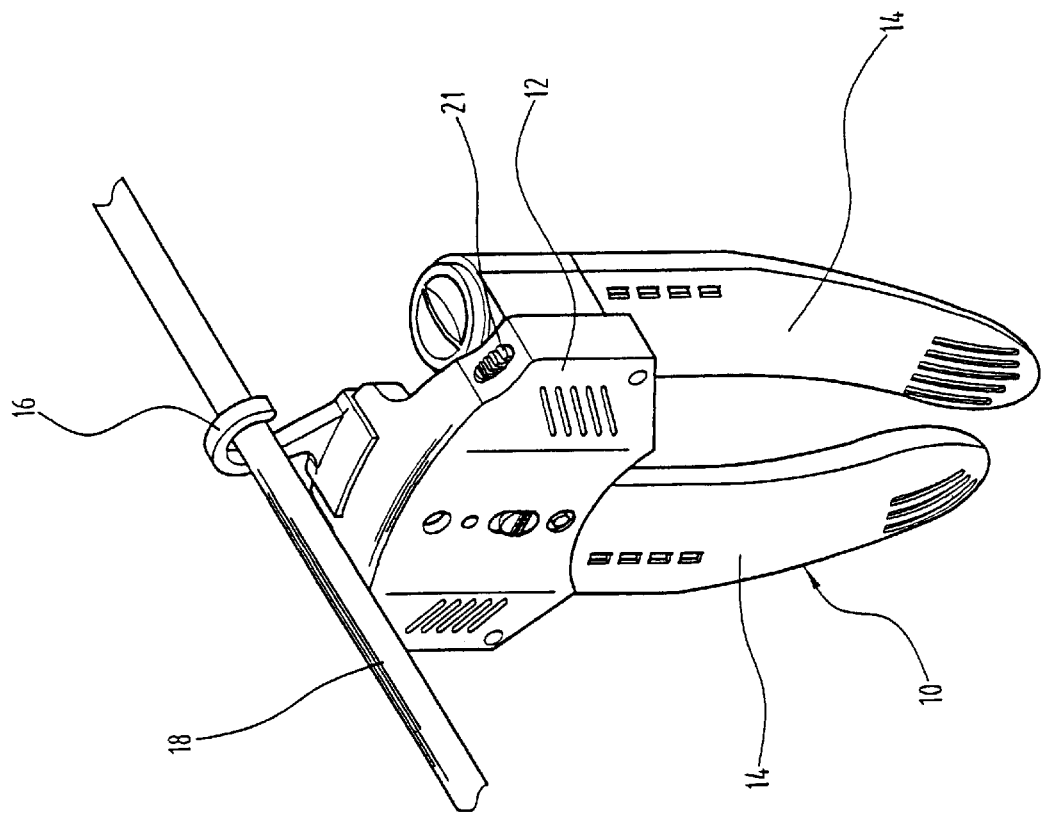
FIG. 6 is a perspective view showing the suit hanger of the present invention serving as a closet air freshener.

FIG. 6 shows a further application of the suit hanger with air freshener of the present invention wherein the arms 14 are moved to the collapsed position and the suit hanger is hung, at a collapsed condition, on a cross bar 18 inside a closet (not shown). Air inside the closet may be refreshed by the air freshener means. Of course, the suit hanger 10 may also be used as a stand-alone device for air cleaning purposes.

Although the present invention has been described with respect to the preferred embodiments, it is contemplated that a variety of modifications, variations and substitutions may be done without departing from the scope of the present invention that is intended to be defined by the appended claims.

What is claimed is:

1. A multi-purpose air freshening device comprising:
   a central casing having at least one air inlet opening for drawing air into;
   an air freshening means which is accommodated in said central casing and generates cleaned air;
   a hook selectively attached to said central casing adapted for hanging on an external fixture;
   a pair of arms attached to opposite sides of said central casing, each defining at least one air outlet opening in communication with said air freshening means adapted to supply said cleaned air to an article hung thereon; and
   a pair of position means providing to pivotally fix said pair of arms at multistage angular positions with respect to said central casing.

2. The multi-purpose air freshening device as claimed in claim 1, wherein said air freshening means having an electric air freshener being powered by a DC/AC power source.

3. The multi-purpose air freshening device as claimed in claim 1, wherein said air freshening means having an electric air freshener being powered by a DC/AC power source and a timer switch which controls the operation of said electric air freshener for a interval of time.

4. The multi-purpose air freshening device as claimed in claim 1, wherein each of said arms having inner space which accommodates at least one battery.

5. The multi-purpose air freshening device as claimed in claim 1, wherein said arms, said central casing and said hook form a suit hanger for hanging clothes, said cleaned air being supplied into said clothes for deodorizing said clothes.

6. The multi-purpose air freshening device as claimed in claim 1, wherein said arms and said central casing form a shoe freshener whereby said cleaned air is driven into said shoes fit over said arms for deodorizing and disinfecting said shoes.

7. The multi-purpose air freshening device as claimed in claim 1, wherein said arms are fixed to said central casing for being moved to a collapsed position to allow said multi-purpose air freshening device to serve as a stand-alone air freshener.

8. The multi-purpose air freshening device as claimed in claim 7, wherein said hook hangs said multi-purpose air freshening device on a cross bar in a closed space.

9. The multi-purpose air freshening device as claimed in claim 1, wherein said hook can be detached from said central casing.

* * * * *